United States Patent [19]

Weinberger et al.

[11] Patent Number: Plant 7,443

[45] Date of Patent: Feb. 12, 1991

[54] PLUM CV. SUPLUMEIGHTEEN

[75] Inventors: John H. Weinberger; Timothy P. Sheehan, both of Fresno, Calif.

[73] Assignee: Sun World, Inc., Indio, Calif.

[21] Appl. No.: 468,516

[22] Filed: Jan. 22, 1990

Related U.S. Application Data

[63] Continuation of Ser. No. 131,177, Dec. 10, 1987, abandoned.

[51] Int. Cl.[5] ..... A01H 5/00

[52] U.S. Cl. ..... Plt./38

[58] Field of Search ..... Plt./38

[56] References Cited

U.S. PATENT DOCUMENTS

| | | | |
|---|---|---|---|
| P.P. 3,164 | 5/1971 | Garabedian | Plt. 38 |
| P.P. 4,621 | 1/1981 | Kitahara et al. | Plt. 38 |
| P.P. 5,342 | 11/1984 | Weinberger | Plt. 38 |
| P.P. 5,413 | 3/1985 | Paul | Plt. 38 |
| P.P. 5,585 | 12/1985 | Peters et al. | Plt. 38 |

*Primary Examiner*—James R. Feyrer

*Attorney, Agent, or Firm*—William H. Elliott, Jr.

[57] ABSTRACT

A plum tree characterized by its unusually large, early ripening fresh quality, red-purple fruit which are round and slightly oblate in shape with prominent lenticels. Trees of the variety are of medium size and bear fruit regularly.

1 Drawing Sheet

This application is a continuation of application Ser. No. 07/131,177, filed Dec. 10, 1987 now abandoned.

This invention relates to the discovery and asexual propagation of a new variety of hybrid plum tree, *Prunus salicina* cv. Suplumeighteen. The tree is an early seasoned red plum bearing fruit of unusually large size cultivated for fresh market use. It was discovered by John H. Weinberger and Timothy P. Sheehan in Fresno, Calif., and has as its seed parent Queen Rosa (unpatented). Its pollen parent is not known.

The new variety cv. Suplumeighteen may be distinguished from other presently available commercial plum cultivars by the following combination of characteristics: Suplumeighteen is a red plum bearing early ripening fresh quality fruit of unusually large size, round and slightly oblate in shape, having prominent lenticels, and a red-purple skin color at full maturity. The new variety holds these distinguishing characteristics through successive asexual propagations by, for example, grafting and budding.

The new variety may be distinguished from its seed parent, Queen Rosa, in the following combination of characteristics: Whereas the skin color of the fruit of Queen Rosa is red, the skin color of the new variety is a deeper red-purple color. Fruit of Suplumeighteen ripens about two weeks earlier than does the fruit of Queen Rosa and its appreciably smaller in size.

The pollen parent of the new variety is not known.

The accompanying drawing illustrates, in full color, a typical stem and leaves of the new plum tree and the ripe fruit is viewed from the stem end and in profile. The drawing also illustrates the fruit sectioned in half from end to end, one-half of the fruit shown with the stone removed from the flesh.

Throughout this specification, color names beginning with a small letter signify that the name of that color, as used in common speech, is aptly descriptive. Color names with capital letters designate values based upon The R.H.S. Colour Chart of The Royal Horticultural Society of London, England.

Plum trees of the new cultivated variety Suplumeighteen have been deposited before the filing date of this application in an orchard located at 5090 East Church Ave., Fresno, Calif. and are identified there by applicant's identification number 401-48.

The descriptive matter which follows pertains to plum trees of the new variety grown in the environment of the San Joaquin Valley and is believed to apply to plants of the variety grown under similar conditions of soil and climate elsewhere.

TREE

The tree is of average size and average vigor. It is upright in habit and vase-formed in shape. The foliage tends towards open growth. The variety is half-hardy. The trees are productive, bearing their fruit regularly.

The trunk is of average thickness and the bark average in texture. The branches are average in caliper and are of medium smoothness. The branches have a dull surface appearance and carry an average number of average-sized lenticels.

LEAVES

In general, leaves are of average size, having an average length of about 9½ cm. and an average width of about 4 cm. Leaves are elliptic in outline and upfolded in profile. Leaf blade tips curve downwardly at an acute angle. The finely serrate leaf margin has no undulation. The leaf apex is cuspidate to broadly acuminate; the leaf base is U-shaped. Leaves are of average thickness.

Leaf color on the upper surface is near Green 137B in color. The upper leaf surface is smooth, with no hairs present and is semi-glossy. The lower leaf surface is near Green 137C in color, weak in glossiness with no hairs present. The lower leaf surface is rugose in texture and has a dull surface appearance.

The petiole is of average length and average thickness. There are usually two medium-sized globose glands positioned on both the leaf base and petiole. Glands are red in color. Stipules are persistent.

Leaf buds are very small and avoid in shape. Their position, relative to the shoot, is slightly held out and their support is small and not decurrent.

Bud burst is early for the class.

Anthocyanin coloration in the flowering shoots is absent. Internode length is average and buds are of average density. Flowering shoots are distributed on spurs, one year old shoots, and older wood. The ratio of wood (leaf) buds to flowering shoots is 1:2.

FLOWERS

Flower buds are average in size and average in length. Their shape is obtuse and positioning is free. Pubescence is abent. Flower bud color is brown.

Flowers attain full bloom, on the average, around the fourth week of February which is early, as compared with similar varieties in the growing area of Fresno, Calif. Duration of bloom is average, about 14 days. The diameter of the fully open flower is average, about 2 cm., and rosaceous in shape. Petals are free. Color of the fully opened flower is White 155D.

Peduncles are of average length and of average thickness, with no hairs.

The receptacle is of average depth. Pubescence of the inner and outer surfaces is absent.

Sepals are positioned adpressed to petals and are ovate in shape. Pubescence of the inner and outer surfaces is absent. There are no flowers bearing double sepals present.

There are no flowers bearing double petals. Petals are of average size, about 0.8 cm., and circular in shape. Claw length is average and there is weak margin waviness present. The base angle is average. The upper petal margin is entirely divided. Pubescence of the inner and outer surfaces is absent. Color of the inner and outer surface is White 155D.

The position of the stigma is level as compared with anthers. Another color just before dehiscence is yellow. Pollen color is yellow. Stamens are perigynous.

Pistils are almost always one in number. Supplementary pistils are absent.

Pubescence is absent in the ovary. Pubescence at the base of the style is absent.

FRUIT

The fruit, as now described, was eating ripe in early June, 1986. The size of the fruit of that stage of its development is uniformly large in size, having an axial diameter of about 5 cm. and a transverse diameter in the suture plane of about 6 cm. Fruit are practically uniform, symmetrical and globose in shape. The position of the maximum diameter is towards the middle. The fruit is symmetric about the suture line. Fruit ripens early in the season and is well adapted for market use and to serve fresh. Keeping quality of the fruit is average and shipping quality is average.

The suture line is distinct and shallow extending from the base but is discontinuous at the apex. The ventral surface is rounded throughout both sides, with equal lips. The apex is slightly depressed. The pistil base does not persist. There is no pubescence at the apex.

The stem cavity is rounded, with the suture showing on one side. The depth of the cavity is about 1½ cm., and its breadth about 1.3 cm. No markings ar present. The base of the fruit is rounded. Its apex is rounded to slightly depressed in shape. The pistil point is apical and slightly depressed in shape.

The stem is of average length, about 1 cm., and adheres strongly to the stone.

The skin, which is of average thickness and of average texture, is tenacious to the flesh and shows no tendency to crack during the dry season. Reticulation is absent. Skin color at maturity is around Red-Purple 59A. Down is wanting and a bloom is present. Skin possesses no roughness.

The color of the flesh is reddish, around Red 46A, and the surface of the pit cavity is near Red 53A. The amygdalin content is wanting and juice is present in abundant to moderate amounts. The flesh has an average sugar content. Flesh texture is average in texture and meaty. Fibers are fine, tender and few in number. Fruit ripens evenly to produce fruit of good eating quality. The flavor is delicate and the aroma wanting. The ratio of stone to flesh is low.

The stone is semi-free, adhering to flesh along both dorsal and ventral edges. Fibers of the stone are short and parts from flesh smoothly, retaining short fiber-like threads along the ridges. The stone is of medium size, being about 2½ cm. in length, and about 2½ cm. in breadth. The width at the stalk end of the stone is about 0.3 cm. and about 1 cm. in thickness. The angle of the stalk end is a right angle. The form of the stone in profile is generally elliptical and cuneate towards the base. The form is ventral view is sub-globular. The stone's base is straight, its apex acuminate. The hilum is oblong. The position of the stone's maximum breadth is toward the middle and the sides are generally equal. The surface of the stone is ridged near the base and there is a partly developed outgrowing keel. The ridges are continuous and jagged towards the base. The ventral stone edge is thin and without a wing throughout. The dorsal stone edge is narrow and shallow with narrow grooves towards the base. The color of the stone is near Orange 26A. The stone has a slight tendency to split during the dry season.

What is claimed is:

1. A new variety of plum tree, the variety being particularly distinguished and characterized by its early-ripening fresh quality fruit of unusually large size, round and slightly oblate in shape, having prominent lenticels, and red-purple skin color at maturity, substantially as herein shown and described.

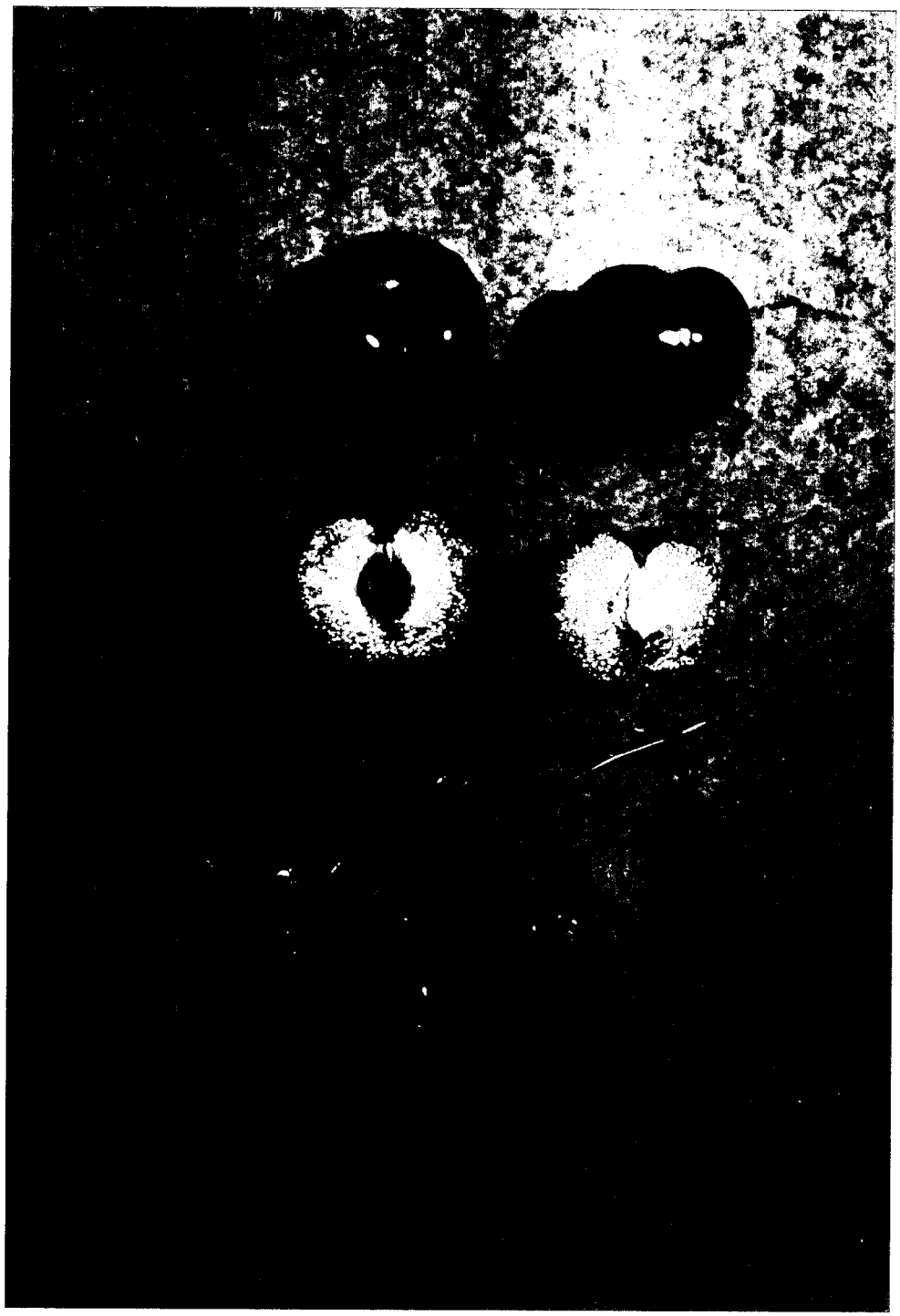

* * * * *